US011951098B2

United States Patent
Miyake et al.

(10) Patent No.: US 11,951,098 B2
(45) Date of Patent: *Apr. 9, 2024

(54) THERAPEUTIC AGENT FOR MEIBOMIAN DYSFUNCTION

(71) Applicant: SANTEN PHARMACEUTICAL CO., LTD., Osaka (JP)

(72) Inventors: Hideki Miyake, Ikoma (JP); Tomoko Oda, Ikoma (JP); Daisuke Shii, Ikoma (JP)

(73) Assignee: SANTEN PHARMACEUTICAL CO., LTD., Osaka (JP)

(*) Notice: Subject to any disclaimer, the term of this patent is extended or adjusted under 35 U.S.C. 154(b) by 0 days.

This patent is subject to a terminal disclaimer.

(21) Appl. No.: 18/170,246

(22) Filed: Feb. 16, 2023

(65) Prior Publication Data

US 2023/0190716 A1 Jun. 22, 2023

Related U.S. Application Data

(60) Continuation of application No. 16/405,249, filed on May 7, 2019, now Pat. No. 11,612,590, which is a division of application No. 15/722,257, filed on Oct. 2, 2017, now abandoned, which is a division of application No. 14/775,019, filed as application No. PCT/JP2014/056416 on Mar. 12, 2014, now abandoned.

(30) Foreign Application Priority Data

Mar. 13, 2013 (JP) .................... 2013-050766

(51) Int. Cl.
A61K 31/436 (2006.01)
A61K 9/00 (2006.01)
A61K 31/675 (2006.01)

(52) U.S. Cl.
CPC .......... *A61K 31/436* (2013.01); *A61K 9/0048* (2013.01); *A61K 31/675* (2013.01)

(58) Field of Classification Search
None
See application file for complete search history.

(56) References Cited

U.S. PATENT DOCUMENTS

| | | | |
|---|---|---|---|
| 6,262,126 B1 | 7/2001 | Meinert | |
| 6,372,243 B2 | 4/2002 | Kobuch et al. | |
| 6,376,517 B1 | 4/2002 | Ross et al. | |
| 6,864,232 B1 | 3/2005 | Ueno | |
| 6,872,383 B2 | 3/2005 | Ueno | |
| 7,001,607 B1 | 2/2006 | Menz et al. | |
| 7,083,802 B2 * | 8/2006 | Peyman ............... | A61P 37/06 424/428 |
| 8,298,569 B2 * | 10/2012 | Philips ................ | A61K 9/1075 424/489 |
| 8,313,763 B2 | 11/2012 | Margaron et al. | |
| 8,367,081 B2 | 2/2013 | Yan et al. | |
| 8,404,641 B2 | 3/2013 | Yan et al. | |
| 8,541,413 B2 | 9/2013 | Wong et al. | |
| 8,614,178 B2 | 12/2013 | Theisinger et al. | |
| 8,765,725 B2 | 7/2014 | Cavanagh et al. | |
| 9,149,470 B2 | 10/2015 | Yan et al. | |
| 9,278,120 B2 | 3/2016 | Cruzat et al. | |
| 9,309,313 B2 | 4/2016 | Dana et al. | |
| 11,612,590 B2 * | 3/2023 | Miyake ............... | A61K 31/436 514/80 |
| 2003/0018044 A1 | 1/2003 | Peyman | |
| 2005/0025810 A1 | 2/2005 | Peyman | |
| 2005/0064010 A1 | 3/2005 | Cooper et al. | |
| 2005/0187241 A1 | 8/2005 | Wen et al. | |
| 2008/0275076 A1 | 11/2008 | Holm et al. | |
| 2009/0092665 A1 | 4/2009 | Mitra et al. | |
| 2009/0221503 A1 | 9/2009 | Kneissel et al. | |
| 2010/0203103 A1 | 8/2010 | Dana et al. | |
| 2011/0028503 A1 | 2/2011 | Taylor et al. | |
| 2011/0104236 A1 | 5/2011 | Dana et al. | |
| 2012/0024177 A1 | 2/2012 | Warner et al. | |
| 2012/0045764 A1 | 2/2012 | Grompe et al. | |
| 2012/0064143 A1 | 3/2012 | Sharp et al. | |
| 2012/0244177 A1 | 9/2012 | Theisinger et al. | |
| 2013/0102572 A1 | 4/2013 | Sugarman | |
| 2013/0273065 A1 | 10/2013 | Dana et al. | |
| 2015/0238605 A1 | 8/2015 | Gnther et al. | |
| 2016/0022648 A1 | 1/2016 | Miyake et al. | |

(Continued)

FOREIGN PATENT DOCUMENTS

| | | |
|---|---|---|
| CA | 2937492 A1 | 5/2010 |
| JP | 2002522485 A | 7/2002 |
| JP | 2005068101 A * | 3/2005 |

(Continued)

OTHER PUBLICATIONS

English language translation of JP 2005 068101 A. (Year: 2005).*
Buech et al., "Formulation of Sirolimus Eye Drops and Corneal Permeation Studies", Journal of Ocular Pharmacology and Therapeutics, 2007, vol. 23, No. 3, pp. 292-303.
Pertsev, et al., Ministry of Health of Ukraine Ukrainian Pharmaceutical Academy, Pharmaceutical and Health Aspects of Drugs, 1999, vol. 1, pp. 106-107, with an English translation. (7 pages).
Office Action issued by the Russian Patent Office dated May 31, 2023, in counterpart Russian Patent Application No. 2019139886, with an English translation of the Office Action. (23 pages).
Office Action dated Jan. 17, 2018, by the Russian Patent Office in corresponding Russian Patent Application No. 2015143511/15 (067184) with partial English translation. (13 pages).

(Continued)

*Primary Examiner* — Dominic Lazaro
(74) *Attorney, Agent, or Firm* — BUCHANAN, INGERSOLL & ROONEY PC

(57) ABSTRACT

A method for suppressing obstruction of meibomian gland in a mammalian subject, the method comprising administering to the mammalian subject an eye drop comprising 0.01 to 0.5% (w/v) of sirolimus or a pharmaceutically acceptable salt thereof as a sole active ingredient, wherein the eye drop is administered to an eye of the mammalian subject 1 to 2 times per day.

12 Claims, No Drawings

(56) References Cited

U.S. PATENT DOCUMENTS

| | | | |
|---|---|---|---|
| 2018/0021314 A1 | 1/2018 | Miyake et al. | |
| 2019/0255026 A1 | 8/2019 | Miyake et al. | |

FOREIGN PATENT DOCUMENTS

| | | | |
|---|---|---|---|
| JP | 2005068101 A | 3/2005 | |
| JP | 2007518690 A | 7/2007 | |
| JP | 2010540682 A | 12/2010 | |
| JP | 2011516400 A | 5/2011 | |
| JP | 2011517659 A | 6/2011 | |
| JP | 2012142160 A | 10/2012 | |
| JP | 2012525154 A | 10/2012 | |
| WO | 9402136 A1 | 2/1994 | |
| WO | 2009025763 A2 | 2/2009 | |
| WO | 2010044893 A1 | 4/2010 | |
| WO | 2012142145 A1 | 10/2012 | |
| WO | 2013126599 A1 | 8/2013 | |
| WO | 2014041071 A1 | 3/2014 | |

OTHER PUBLICATIONS

Office Action dated Sep. 15, 2017, by the Russian Patent Office in corresponding Russian Patent Application No. 2015143511/15 (067184) with partial English translation. (14 pages).

Amano et al., "Definition and Diagnostic Criteria for Meibomian Gland Dysfunction", Journal of the Eye, 2010, pp. 627-631, vol. 27, No. 5.

Barber et al., "Phase III Safety Evaluation of Cyclosporine 0.1 % Ophthalmic Emulsion Administered Twice Daily to Dry Eye Disease Patients for Up to 3 Years", Ophthalmology, 2005, pp. 1790-1794, vol. 112, No. 10.

Extended Search Report dated Sep. 28, 2016, by the European Patent Office for Application No. EP14763999.1. (9 pages).

Hamrah et al., "Meibomian gland dysfunction," abstract of WO 2013126599, AN: 2013:1339350, HCAPLUS, ON: 159:412072.

Javadi et al., "Dry Eye Syndrome", Journal of Ophthalmic and Vision Research, 2011, pp. 192-198, vol. 6, No. 3.

Khandelwal et al., "Androgen regulation of gene expression in human meibomian gland and conjunctival epithelial cells", Molecular Vision, 2012, pp. 1055-1067, vol. 18.

Wang et al., "Effect assessment of subconjunctival injection of rapamycin-loaded microspheres In non-obese diabetic mice with dry eye caused by Sjogren's syndrome", Int Eye Sci, 2013, pp. 861-864, vol. 13, No. 5 (with English abstract).

Maychuk et al., "Classification of meibomian gland dysfunction combined with the dry eye syndrome pathoaenetical approaches in the combination therapy", Russian Medical Journal, 7 pages, vol. 4, No. 169.

McKown et al., "Lacritin and other new proteins of the lacrimal functional unit", Experimental Eye Research, 2009, pp. 848-858, vol. 88, No. 5.

Nelson et al., "The International Workshop on Meibomian Gland Dysfunction: Report of the Definition and Classification Subcommittee", Investigative Ophthalmology & Visual Science, 2011, pp. 1930-1937, vol. 52, No. 4.

International Search Report dated Jun. 3, 2014, by the Japanese Patent Office for Application No. PCT/JP2014/056416. (3 pages).

Written Opinion dated Jun. 3, 2014, by the Japanese Patent Office for Application No. PCT/JP2014/056416. (4 pages).

\* cited by examiner

THERAPEUTIC AGENT FOR MEIBOMIAN DYSFUNCTION

CROSS-REFERENCE TO RELATED APPLICATIONS

This application is a continuation of U.S. patent application Ser. No. 16/405,249, filed May 7, 2019, now U.S. Pat. No. 11,612,590, which is a divisional of U.S. application Ser. No. 15/722,257, filed Oct. 2, 2017, now abandoned, which is a divisional of U.S. application Ser. No. 14/775,019, filed Sep. 11, 2015, now abandoned, which is a U.S. national stage application of PCT/JP2014/056416, filed Mar. 12, 2014, which claims priority to Japanese Patent Application No. 2013-050766, filed Mar. 13, 2013, the entire contents of all of which are hereby incorporated by reference.

TECHNICAL FIELD

The present invention relates to a prophylactic and/or therapeutic agent for meibomian gland dysfunction containing a compound represented by the formula (1):

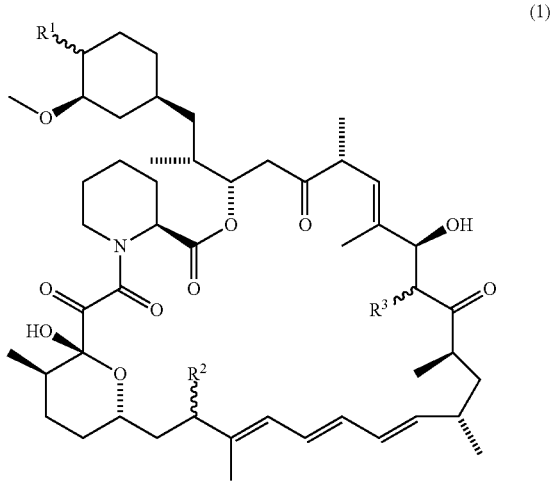

wherein
- $R^1$ represents a hydroxyl group, a methoxy group, a hydroxymethoxy group, an ethoxy group, a 1-hydroxyethoxy group, a 2-hydroxyethoxy group, a 2-methoxyethoxy group, a 2-ethoxyethoxy group, a formyloxy group, a carboxyoxy group, an acetoxy group, a hydroxyacetoxy group, a propionyloxy group, a 2-hydroxypropionyloxy group, a 3-hydroxypropionyloxy group, a 2-methylpropionyloxy group, a 2-(hydroxymethyl)-propionyloxy group, a 3-hydroxy-2-(hydroxymethyl)propionyloxy group, a 2,2-dimethylpropionyloxy group, a 2-(hydroxymethyl)-2-methylpropionyloxy group, a 2,2-bis(hydroxymethyl)propionyloxy group, a methylphosphynoyloxy group, a dimethylphosphynoyloxy group or a 1H-tetrazol-1-yl group;
- $R^2$ represents a hydrogen atom, a hydroxyl group, a methoxy group, a mercapto group or a methylthio group;
- $R^3$ represents a hydrogen atom, a hydroxyl group or a methoxy group;
- a wavy line represents that the carbon atom bonded to $R^1$, $R^2$ or $R^3$ can take either configuration of S or R;

(hereinafter sometimes referred to as "the present compound") or a pharmaceutically acceptable salt thereof as an active ingredient.

BACKGROUND ART

The meibomian gland is present in the tarsus, is a sebaceous gland having orifices at the upper and lower eyelid margins, and a lipid secreted by the meibomian gland plays a variety of roles in the external eye.

In Non-Patent Document 1, it has been disclosed that among the patients visiting ophthalmology who appeal symptoms such as ocular discomfort, as a main complaint, meibomian gland dysfunction (hereinafter also referred to as "MGD") becomes a cause thereof in a significant proportion, and lowering in quality of life is caused in many patients.

However, it has never been known an effective treatment method of MGD, and yet, clear definition for MGD or diagnostic criteria itself has never been present in the first place. Thus, in recent years, there are worldwide movements to define MGD as an independent disease and to prepare its diagnostic criteria, and in Japan, MGD has been defined to be a disease "which is a state in which the function of the meibomian gland causes abnormality in diffuse by various causes, and is accompanied by chronic ocular discomfort" (see Non-Patent Document 1).

Also, in Non-Patent Document 1, it has been disclosed that MGD is classified into a decreased secretion type MGD and an increased secretion type MGD, and in the decreased secretion type MGD, it has also been disclosed that secretion of meibomian gland lipids is reduced by obstruction of the meibomian gland orifices and the like. Further, in Non-Patent Document 1, it has been also disclosed that three of <1> subjective symptom such as ocular discomfort, <2> signs/findings on abnormalities around the meibomian gland orifices such as vasodilation, and <3> signs/findings on obstruction at the meibomian gland orifices are positive is diagnosed to be a decreased secretion type MGD.

Incidentally, as a disease generating at the meibomian gland, chalazion, internal hordeolum, etc., have been known other than MGD, and in Non-Patent Document 1, there are disclosed that these diseases are topical diseases, and are different diseases from MGD in which the meibomian gland is obstructed in diffuse. In addition, MGD sometimes causes an evaporation promoting type dry eye, in Non-Patent Document 1, it has been disclosed that there is a case where no dry eye is accompanied depending on an amount of tear fluid, a term of the disease or a degree of severity.

In Non-Patent Document 2, a classification method of MGD in the U.S. has been disclosed, and it has also been disclosed that the decreased secretion type MGD (low-delivery state MGD) can be further classified into two of "hyposecretory MGD (meibomian hyposecretion)" and "obstructive MGD (meibomian gland obstruction)". Further, in Non-Patent Document 2, it has been suggested that MGD is one of the diseases which cause posterior blepharitis.

Sirolimus (also referred to as rapamycin) has been known to be an immunosuppressant, and has been used as an oral preparation in the U.S., etc. It has also been known that a derivative (hereinafter sometimes referred to as "sirolimus derivative") in which a part of the structure of sirolimus has been modified has the similar activity to that of the sirolimus, and in the sirolimus derivative, deforolimus, everolimus, temsirolimus, zotarolimus, biolimus, novolimus, etc., are contained.

In Patent Document 1, it has been disclosed an ophthalmic composition comprising an mTOR inhibitor such as sirolimus, everolimus, temsirolimus, etc., a first surfactant having an HLB index exceeding about 10, and a second surfactant having an HLB index exceeding about 13. However, in Patent Document 1, it has never been disclosed whether the mTOR inhibitor has a treatment effect on MGD or not.

Also, in Patent Document 2, it has been suggested that a pipecolic acid derivative such as rapamycin, can treat vision disorder, and in the vision disorder, meibomian gland carcinoma and internal hordeolum (meibomian gland sty) are contained. However, the meibomian gland carcinoma is a disease clearly different from MGD, and as stated above, the internal hordeolum is a disease also different from MGD.

As mentioned above, in Patent Document 1 and 2, there is neither description nor suggestion on whether the present compound has a treatment effect on MGD or not.

In addition, it is also not clear for those skilled in the art whether or not a medicament which can treat dry eye or posterior blepharitis can prevent and/or treat MGD itself.

PRIOR ART DOCUMENTS

Patent Documents

Patent Document 1: JP 2010-540682A
Patent Document 2: JP 2002-522485A

Non-Patent Documents

Non-Patent Document 1: Journal of the Eye, 27(5), 627-631 (2010)
Non-Patent Document 2: Investigative Ophthalmology & Visual Science, 52(4), 1930-1937 (2011)

DISCLOSURE OF THE INVENTION

Problems to be Solved by the Invention

An object of the present invention is to provide a prophylactic and/or therapeutic agent for meibomian gland dysfunction (MGD).

Means to Solve the Problems

The present inventors have intensively studied to search a prophylactic and/or therapeutic agent for meibomian gland dysfunction (MGD), and as a result, they have found that a compound represented by the formula (1):

wherein
$R^1$ represents a hydroxyl group, a methoxy group, hydroxymethoxy group, ethoxy group, 1-hydroxyethoxy group, 2-hydroxyethoxy group, 2-methoxyethoxy group, 2-ethoxyethoxy group, a formyloxy group, a carboxyoxy group, an acetoxy group, a hydroxyacetoxy group, a propionyloxy group, a 2-hydroxypropionyloxy group, a 3-hydroxypropionyloxy group, a 2-methylpropionyloxy group, a 2-(hydroxymethyl)-propionyloxy group, a 3-hydroxy-2-(hydroxymethyl)propionyloxy group, a 2,2-dimethylpropionyloxy group, a 2-(hydroxymethyl)-2-methylpropionyloxy group, a 2,2-bis(hydroxymethyl)propionyloxy group, a methylphosphynoyloxy group, a dimethylphosphynoyloxy group or a 1H-tetrazol-1-yl group;
$R^2$ represents a hydrogen atom, a hydroxyl group, a methoxy group, a mercapto group or a methylthio group;
$R^3$ represents a hydrogen atom, a hydroxyl group or a methoxy group;
a wavy line represents that the carbon atom bonded to $R^1$, $R^2$ or $R^3$ can take either configuration of S or R,
or a pharmaceutically acceptable salt thereof can reduce a number of obstructions at the meibomian gland orifices, and the compound of the above-mentioned formula (1) or a pharmaceutically acceptable salt thereof has a treatment effect on MGD and suppresses obstruction of the meibomian gland, whereby the present invention has been accomplished.

That is, the present invention relates to a prophylactic and/or therapeutic agent for meibomian gland dysfunction (MGD), which comprises the compound of the above-mentioned formula (1) (the present compound) or a pharmaceutically acceptable salt thereof as an active ingredient (hereinafter sometimes referred to as "the present agent").

Also, the present compound is preferably a compound, in the above-mentioned formula (1), wherein $R^1$ represents a hydroxyl group, a 2-hydroxyethoxy group, a 2-ethoxyethoxy group, a 2,2-bis(hydroxymethyl)propionyloxy group, a dimethyl-phosphynoyloxy group or a 1H-tetrazol-1-yl group; $R^2$ represents a hydrogen atom, a hydroxyl group, a methoxy group or a methylthio group; and $R^3$ represents a hydrogen atom or a methoxy group, or a pharmaceutically acceptable salt thereof.

Further, the present compound is preferably a compound, in the above-mentioned formula (1), wherein $R^1$ represents a hydroxyl group or a dimethyl-phosphynoyloxy group; $R^2$ represents a methoxy group; $R^3$ represents a methoxy group, or a pharmaceutically acceptable salt thereof.

Moreover, the present compound is preferably sirolimus, deforolimus, everolimus, temsirolimus, zotarolimus, biolimus, novolimus, 7-epi-rapamycin, 7-thiomethyl-rapamycin, 7-epi-thiomethyl-rapamycin, 7-demethoxy-rapamycin, 32-demethoxy-rapamycin or their pharmaceutically acceptable salts, particularly preferably sirolimus, deforolimus or a salt thereof.

Furthermore, an administration form of the present agent is preferably instillation administration or administration to the eyelid skin.

Also, a dosage form of the present agent is preferably an eye drop, an ophthalmic ointment or an ointment (excluding an ophthalmic ointment), and characteristics of the eye drop is preferably a suspension or an emulsion.

Further, other embodiments of the present invention relate to a composition for suppressing obstruction of the meibomian gland which comprises the present compound or a pharmaceutically acceptable salt thereof as an active ingredient (hereinafter sometimes referred to as "the present composition").

Moreover, an active ingredient of the present composition is preferably sirolimus, deforolimus or a salt thereof.

Furthermore, other embodiments of the present invention relate to a pharmaceutical composition for prophylaxis and/or treatment of meibomian gland dysfunction (MGD) which comprises the compound of the above-mentioned formula (1) (the present compound) or a pharmaceutically acceptable salt thereof, and a pharmaceutically acceptable additive.

Also, other embodiments of the present invention relate to the compound of the above-mentioned formula (1) (the present compound) for use in the suppression of obstruction of the meibomian gland.

Further, other embodiments of the present invention relate to the compound of the above-mentioned formula (1) (the present compound) for use in the suppression of telangiectasia around the meibomian gland orifices.

Moreover, other embodiments of the present invention relate to the compound of the above-mentioned formula (1) (the present compound) for use in the prophylaxis and/or treatment of meibomian gland dysfunction (MGD).

Furthermore, other embodiments of the present invention relate to a use of the compound of the above-mentioned formula (1) (the present compound) for the manufacture of a composition for suppressing obstruction of the meibomian gland.

Also, other embodiments of the present invention relate to a use of the compound of the above-mentioned formula (1) (the present compound) for the manufacture of a composition for suppressing telangiectasia around the meibomian gland orifices.

Further, other embodiments of the present invention relate to a use of the compound of the above-mentioned formula (1) (the present compound) for the manufacture of a medicine for prophylaxis and/or treatment of meibomian gland dysfunction (MGD).

Moreover, other embodiments of the present invention relate to a method for suppressing obstruction of meibomian gland, which comprises administering the compound of the above-mentioned formula (1) (the present compound) to a human or an animal.

Furthermore, other embodiments of the present invention relate to a method for suppressing telangiectasia around the meibomian gland orifices, which comprises administering the compound of the above-mentioned formula (1) (the present compound) to a human or an animal.

Still further, other embodiments of the present invention relate to a method for prophylaxis and/or treatment of meibomian gland dysfunction (MGD), which comprises administering the compound of the above-mentioned formula (1) (the present compound) to a human or an animal.

Effects of the Invention

The compound of the above-mentioned formula (1) or a pharmaceutically acceptable salt thereof is useful as a prophylactic and/or therapeutic agent for meibomian gland dysfunction (MGD).

BEST MODE TO CARRY OUT THE INVENTION (A) The present compound is a compound in which the respective groups are the groups shown below in the compound represented by the formula (1):

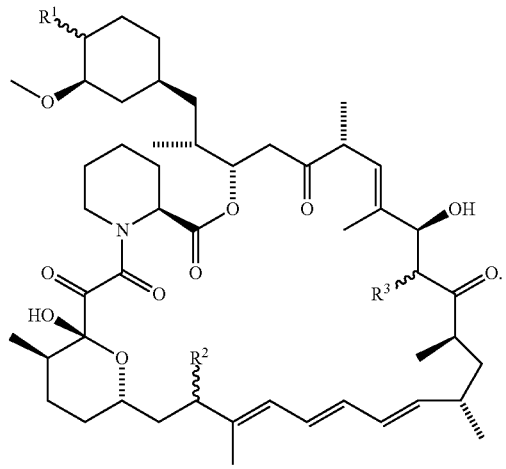

(A1) $R^1$ represents a hydroxyl group, a methoxy group, a hydroxymethoxy group, an ethoxy group, a 1-hydroxyethoxy group, a 2-hydroxyethoxy group, a 2-methoxyethoxy group, a 2-ethoxyethoxy group, a formyloxy group, a carboxyoxy group, an acetoxy group, a hydroxyacetoxy group, a propionyloxy group, a 2-hydroxypropionyloxy group, a 3-hydroxypropionyloxy group, a 2-methylpropionyloxy group, a 2-(hydroxymethyl)propionyloxy group, a 3-hydroxy-2-(hydroxymethyl)propionyloxy group, a 2,2-dimethylpropionyloxy group, a 2-(hydroxymethyl)-2-methylpropionyloxy group, a 2,2-bis(hydroxymethyl)propionyloxy group, a methylphosphynoyloxy group, a dimethylphosphynoyloxy group or a 1H-tetrazol-1-yl group;

(A2) $R^2$ represents a hydrogen atom, a hydroxyl group, a methoxy group, a mercapto group, a methylthio group, a phenyl group, a 2,4,6-trihydroxyphenyl group or a 2,4,6-trimethoxyphenyl group; and (A3) $R^3$ represents a hydrogen atom, a hydroxyl group or a methoxy group.

That is, the present compound is a material in which the respective group enumerated in the above-mentioned (A1), (A2) and (A3) are combined in the compound represented by the above-mentioned formula (1).

(B) As a preferred example of the present compound, there may be mentioned a compound wherein the respective groups are the groups shown below in the compound represented by the above-mentioned formula (1).

(B1) $R^1$ represents a hydroxyl group, a 2-hydroxyethoxy group, a 2-ethoxy-ethoxy group, a 2,2-bis(hydroxymethyl)propionyloxy group, a dimethylphosphynoyloxy group or a 1H-tetrazol-1-yl group;

(B2) $R^2$ represents a hydrogen atom, a hydroxyl group, a methoxy group, a methylthio group or a 2,4,6-trimethoxyphenyl group; and (B3) $R^3$ represents a hydrogen atom or a methoxy group.

That is, a preferred example of the present compound is a material in which the respective group enumerated in the above-mentioned (B1), (B2) and (B3) are combined in the above-mentioned formula (1).

(C) As a more preferred example of the present compound, there may be mentioned a compound in which the respective groups are groups mentioned below in the above-mentioned formula (1).

(C1) R¹ represents a hydroxyl group, a 2-hydroxyethoxy group, a 2-ethoxy-ethoxy group, a 2,2-bis(hydroxymethyl)propionyloxy group or a dimethylphosphynoyloxy group;

(C2) R² represents a methoxy group;

(C3) R³ represents a methoxy group;

That is, a more preferred example of the present compound is a material in which the respective groups enumerated in the above-mentioned (C1), (C2) and (C3) are combined in the compound represented by the above-mentioned formula (1).

In the above-mentioned formula (1), a wavy line represents that the carbon atom bonded to R¹, R² or R³ can take either configuration of S or R, and in the present invention, the carbon atom bonded to R¹ preferably has an R-configuration, and when R² or R³ is not a hydrogen atom, the carbon atom bonded to R² preferably has an S-configuration, and the carbon atom bonded to R³ preferably has an R-configuration.

Specific examples of the present compound may be mentioned the following compounds.

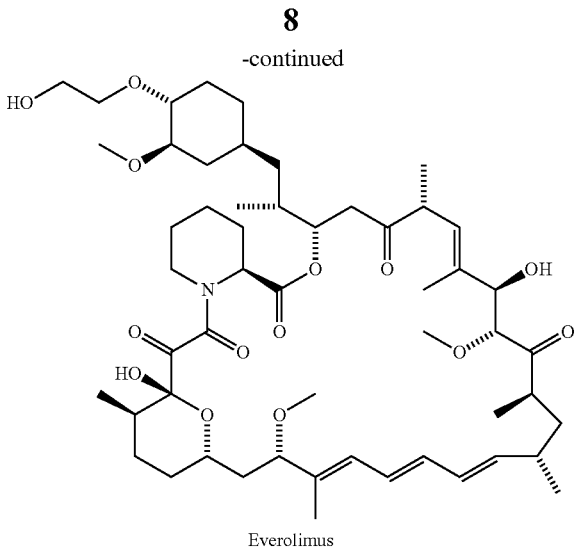

Everolimus

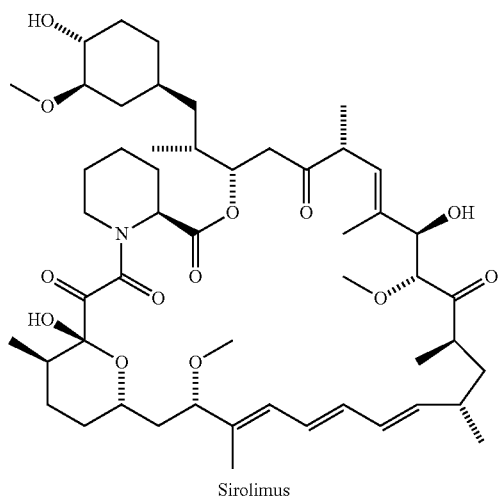

Sirolimus

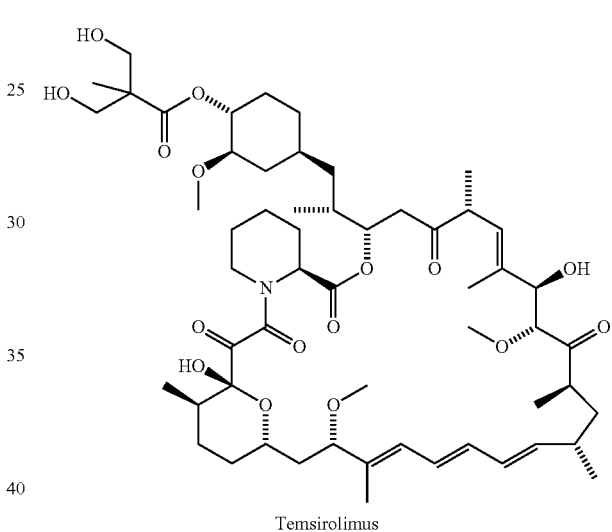

Temsirolimus

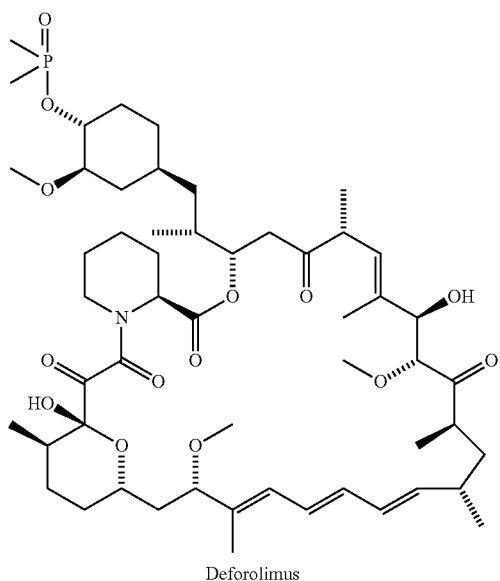

Deforolimus

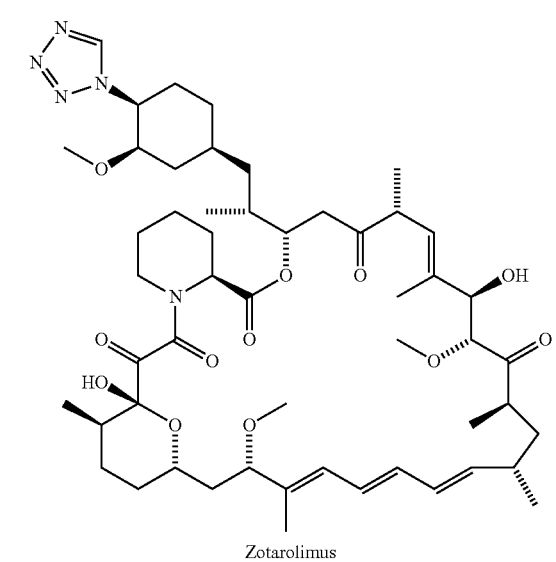

Zotarolimus

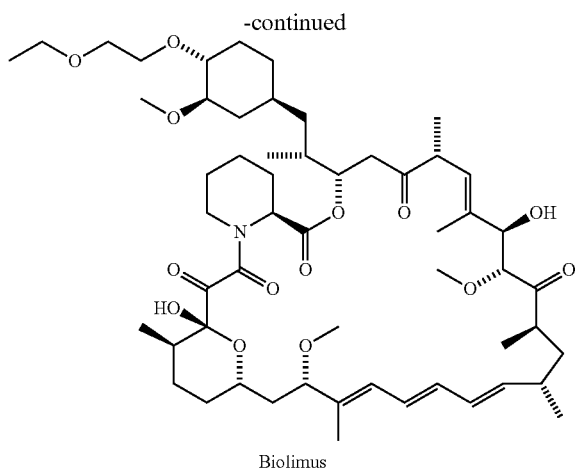
Biolimus
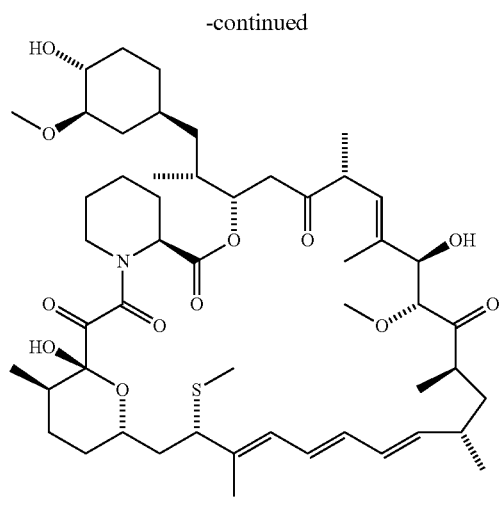
7-Thiomethyl-rapamycin
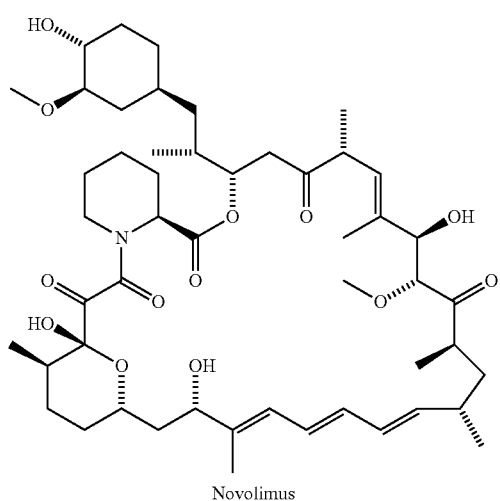
Novolimus
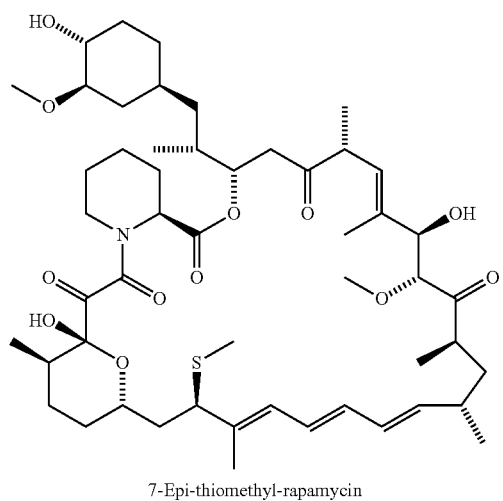
7-Epi-thiomethyl-rapamycin
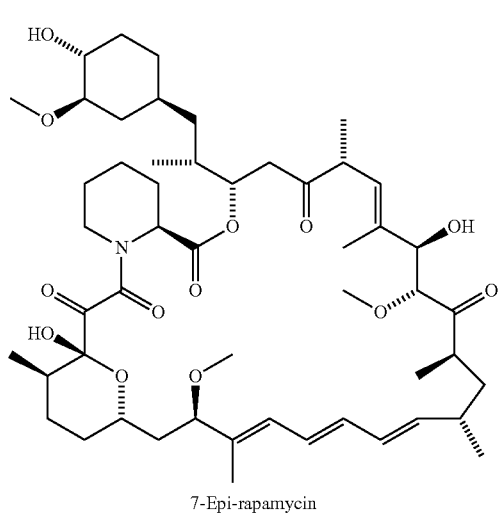
7-Epi-rapamycin
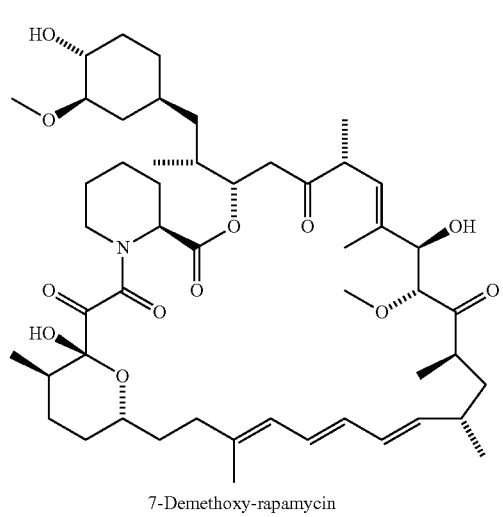
7-Demethoxy-rapamycin

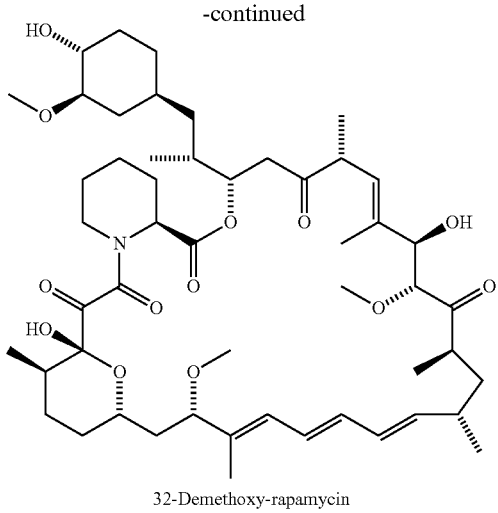

32-Demethoxy-rapamycin

Preferred specific examples of the present compound are sirolimus or deforolimus, and sirolimus is particularly preferred.

The present compound or a pharmaceutically acceptable salt thereof can be prepared in accordance with the usual method in the field of the organic synthetic chemistry, and in particular, with regard to sirolimus, that commercially available from LKT laboratories, Inc., (Catalog number: R0161) may be used. In addition, with regard to deforolimus, it may be prepared in accordance with the method disclosed in JP 2005-516065A.

The pharmaceutically acceptable salt of the present compound may be mentioned, for example, a salt with an inorganic acid such as hydrochloric acid, hydrobromic acid, hydroiodic acid, nitric acid, sulfuric acid and phosphoric acid; a salt with an organic acid such as acetic acid, fumaric acid, maleic acid, succinic acid, citric acid, tartaric acid, adipic acid, gluconic acid, glucoheptonic acid, glucuronic acid, terephthalic acid, methanesulfonic acid, lactic acid, hippuric acid, 1,2-ethanedisulfonic acid, isethionic acid, lactobionic acid, oleic acid, pamoic acid, polygalacturonic acid, stearic acid, tannic acid, trifluoromethanesulfonic acid, benzenesulfonic acid, p-toluenesulfonic acid, lauryl sulfate, methyl sulfate, naphthalenesulfonic acid and sulfosalicylic acid; a quaternary ammonium salt with methyl bromide and methyl iodide; and a salt with a halogen ion including a bromine ion, a chlorine ion and an iodine ion.

Also, the present compound or a pharmaceutically acceptable salt may take a form of a hydrate or a solvate.

When a geometric isomer or an optical isomer exists in the present compound or a pharmaceutically acceptable salt thereof, the isomer(s) or a salt thereof is/are also included in the scope of the present invention. In addition, when a proton tautomerism exists in the present compound or a pharmaceutically acceptable salt thereof, the tautomer(s) or a salt thereof is/are also included in the scope of the present invention.

When crystal polymorphism and a crystal polymorphism group (crystal polymorphism system) exist in the present compound or a pharmaceutically acceptable salt (including a hydrate or a solvate), these crystal polymorphs and crystal polymorphism group (crystal polymorphism system) are also included in the scope of the present invention. Here, the crystal polymorphism group (crystal polymorphism system) means a crystal form at the respective stages when the crystal form is changed by the conditions and states of preparation, crystallization, preservation, etc., of these crystals (incidentally, the state after formulation is also contained in the above states), and the whole processes.

The present compound or a pharmaceutically acceptable salt thereof can be used for a prophylaxis and/or a treatment of meibomian gland dysfunction (MGD).

The definition of the meibomian gland dysfunction (MGD) is, for example, "a state in which the function of the meibomian gland causes abnormality in diffuse by various causes, which is accompanied by chronic ocular discomfort." Here, "the state in which the function of the meibomian gland causes abnormality in diffuse" means that, for example, not topical meibomian gland abnormality recognized in chalazion, internal hordeolum, etc., but meibomian gland abnormality such as telangiectasia, obstruction at the meibomian gland orifices, etc., is recognized in diffuse. Also, MGD is classified into a decreased secretion type MGD (low-delivery state) and an increased secretion type MGD (high delivery state), further as the decreased secretion type MGD (low-delivery state MGD), there may be mentioned "hyposecretory MGD (meibomian hyposecretion)" and "obstructive MGD (meibomian gland obstruction)".

In the decreased secretion type MGD, secretion of meibomian gland lipids is reduced by obstruction at the meibomian gland orifices, etc. Also, in the increased secretion type MGD, secretion of meibomian gland lipids is increased by various causes.

On the other hand, a state in which obstruction of the meibomian gland orifices can be admitted, but no subjective symptom is accompanied is sometimes called as, for example, "meibomian gland infarction (meibomian gland concretion)", and the meibomian gland infarction is also included and in MGD of the present invention.

As MGD which can be treated by the present compound or a pharmaceutically acceptable salt thereof, particularly preferred is the decreased secretion type MGD.

By the way, as explained at the column of the background art, MGD sometimes becomes a cause of the dry eye, and has a possibility of causing posterior blepharitis.

The MGD contains "MGD which is accompanied by dry eye and/or posterior blepharitis (complicated)", "MGD which becomes a cause of dry eye and/or posterior blepharitis", "MGD which is not accompanied by dry eye (not complicated)", "MGD which does not become a cause of dry eye", "MGD which is not accompanied by posterior blepharitis (not complicated)", and "MGD which does not become a cause of posterior blepharitis".

In the present invention, "prophylactic and/or therapeutic agent for MGD" means a medicine which prevents and/or treats MGD. Here, "to treat and/or prevent MGD" means that, among the three indexes admitted by the MGD patient disclosed in the above-mentioned Non-Patent Document 1 (<1> subjective symptom such as ocular discomfort, <2> signs/findings on abnormalities around the meibomian gland orifices such as vasodilation, and <3> signs/findings on obstruction at the meibomian gland orifices), at least an improvement in "signs/findings on obstruction at the meibomian gland orifices" can be recognized, preferably improvements in "signs/findings on abnormalities around the meibomian gland orifices such as vasodilation" and "signs/findings on obstruction at the meibomian gland orifices" can be recognized.

Improvement in "signs/findings on abnormalities around the meibomian gland orifices such as vasodilation" means that, for example, telangiectasia around the meibomian gland orifices is suppressed, etc.

In the present invention, "suppressing telangiectasia around the meibomian gland orifices" means that, for example, "signs/findings on abnormalities around the meibomian gland orifices signs/findings of vasodilation" is to be resolved.

Improvement in "signs/findings on obstruction at the meibomian gland orifices" means that, for example, obstruction of the meibomian gland orifices is suppressed.

In the present invention, "suppressing obstruction of the meibomian gland" means that, for example, "signs/findings on obstruction at the meibomian gland orifices" is to be resolved.

In the present invention, the present agent or the present composition may contain an active ingredient other than the present compound or a pharmaceutically acceptable salt thereof, and may contain the present compound or a pharmaceutically acceptable salt thereof as a sole active ingredient.

In the present invention, the present agent or the present composition can be administered to the patient by, for example, orally or parenterally, and preferably administered by parenterally. As a parenteral administration form, there may be mentioned instillation administration (including instillation of an ophthalmic ointment), subconjunctival administration, administration to the interior of the conjunctival sac, administration under the Tenon's capsule, etc., and instillation administration is particularly preferred.

In addition, the parenteral administration form may also contain, for example, dermal administration, and in the dermal administration according to the present invention, administration to the eyelid skin is particularly preferred.

In the present invention, the preparation containing the compound of the present invention or pharmaceutically acceptable salt thereof as an active ingredient is formulated into a dosage form suitable for administration with a pharmaceutically acceptable additive, if necessary. The dosage form suitable for the oral administration may be mentioned, for example, capsules, fine granules, granules, powders, pills, tablets, etc. Also, the dosage form suitable for parenteral administration may be mentioned, for example, eye drops, ophthalmic ointments, ointments (excluding ophthalmic ointments), injections, a preparation for intraocular implant (including punctual plug), intercalating agents, plasters, gels, etc. Incidentally, these can be prepared by using usual techniques generally used in the field of the art. Moreover, the present compound or a pharmaceutically acceptable salt thereof can be made a formulation which is made like DDS (drug delivery system) such as a microsphere.

As stated above, the present agent or the present composition is preferably subjected to instillation administration, so that the preferred dosage form of the present agent or the present composition is eye drops or ophthalmic ointments, and eye drops are particularly preferred. Incidentally, when the present compound or a pharmaceutically acceptable salt thereof is prepared as the eye drops, characteristics of the eye drops may be a dissolved type solution (dissolved type eye drops), a suspension (suspended type eye drops), or an emulsion (emulsion eye drops), preferably a suspension or an emulsion.

Also, as stated above, the present agent or the present composition is preferably subjected to administration to the eyelid skin, so that the preferred dosage form of the present agent or the present composition is ointments (excluding ophthalmic ointments).

To the present compound or a pharmaceutically acceptable salt thereof may be added by optionally selecting, for example, an excipient such as microcrystalline cellulose, lactose, glucose, D-mannitol, anhydrous dibasic calcium phosphate, starch and sucrose; a disintegrator such as carboxymethyl cellulose, calcium carboxymethyl cellulose, croscarmellose sodium, crospovidone, starch, partially pregelatinized starch and low substituted degree hydroxypropyl cellulose; a binder such as hydroxypropyl cellulose, ethyl cellulose, gum Arabic, starch, partially pregelatinized starch, polyvinylpyrrolidone and polyvinyl alcohol; a lubricant such as magnesium stearate, calcium stearate, talc, hydrated silicon dioxide and hydrogenated oil; a coating agent such as refined white sugar, hydroxypropylmethyl cellulose, hydroxypropyl cellulose, methyl cellulose, ethyl cellulose and polyvinylpyrrolidone; a corrigent such as citric acid, aspartame, ascorbic acid and menthol, to prepare capsules, fine granules, granules, powders, pills or tablets.

In the present invention, the eye drops can be prepared by selecting and using, for example, an oil component such as medium chain fatty acid triglyceride (MCT); an isotonicifier such as sodium chloride, potassium chloride and glycerin; a buffering agent such as sodium phosphate, sodium acetate and ε-aminocaproic acid; a surfactant such as tyloxapol, poloxamer 188, polyoxyethylene sorbitan monooleate, polyoxyl 40 stearate and polyoxyethylene hardened castor oil; a stabilizer such as sodium citrate and sodium edetate; a preservative such as benzalkonium chloride and paraben, depending on necessity. A pH of the eye drops may be within the range acceptable for an ophthalmic preparation, and it is usually preferred in the range of 4 to 8.

In the present invention, ophthalmic ointments or ointments (excluding ophthalmic ointments) can be prepared by using a generally used base, for example, white petrolatum, liquid paraffin, etc.

In the present invention, the injections can be prepared by selecting and using, for example, an isotonicifier such as sodium chloride; a buffering agent such as sodium phosphate; a surfactant such as polyoxyethylene sorbitan monooleate; a thickener such as methyl cellulose, depending on necessity.

In the present invention, the preparation for intraocular implant can be prepared by using, for example, a biodegradable polymer such as a polylactic acid, a polyglycolic acid, a lactic acid-glycolic acid copolymer and a hydroxypropyl cellulose.

In the present invention, the intercalating agents can be prepared by pulverizing and mixing, for example, a biodegradable polymer such as hydroxypropyl cellulose, hydroxypropylmethyl cellulose, carboxyvinyl polymer and polyacrylic acid, with the present compound, and compression-molding the powder, and if necessary, an excipient, a binder, a stabilizer and/or a pH adjuster may be used.

In the present invention, an administration dose of the present compound or a pharmaceutically acceptable salt thereof may be optionally changed depending on a dosage form, severity of the symptoms, an age or a body weight of a patient to be administered, and a judgment of a doctor, etc., and, for example, it can be generally administered to an adult person per a day of 0.000001 to 1,000 mg once or divided into several times.

When the present compound or a pharmaceutically acceptable salt thereof is to be applied to the eyes as eye drops, for example, the eye drops with a concentration of the active ingredient of 0.0001 to 1% (w/v), preferably 0.001 to 1% (w/v), more preferably 0.01 to 0.5% (w/v) can be applied to the eyes of an adult person once a day or divided into several times, preferably 1 to 2 times per a day, more preferably once a day.

When the present compound or a pharmaceutically acceptable salt thereof is to be applied to the eyes (instillation) as ophthalmic ointments, or to be administered to the eyelid skin as ointments (excluding ophthalmic ointments), for example, the ophthalmic ointment with a concentration of the active ingredient of 0.0001 to 1% (w/w), preferably 0.001 to 1% (w/w), more preferably 0.01 to 0.5% (w/w) can be applied to the eyes (instillation) or administered to the eyelid skin of an adult person once a day or divided into several times.

When the present compound or a pharmaceutically acceptable salt thereof is administered as the injections, for example, the injection containing 0.000001 to 1,000 mg of an active ingredient can be administered to an adult person per a day once or divided into several times.

When the present compound or a pharmaceutically acceptable salt thereof is administered as the preparation for intraocular implant, for example, the preparation for intraocular implant containing 0.000001 to 1,000 mg of an active ingredient can be implanted to an adult person.

When the present compound or a pharmaceutically acceptable salt thereof is administered as the intercalating agents, for example, the intercalating agent containing 0.000001 to 1,000 mg of an active ingredient can be intercalated to an adult person.

In the following, the results of Pharmacological tests and Preparation examples are shown, and these examples are intended to better understand the present invention and not to limit the scope of the present invention.

EXAMPLES

Test Using Complete Freund's Adjuvant Administered Rabbit

In a complete Freund's adjuvant administered rabbit, telangiectasia around the meibomian gland orifices, and obstruction at the meibomian gland orifices, which are similar to the signs/findings of MGD can be recognized. Effects of sirolimus which was a representative example of the present compound on the telangiectasia and obstruction were investigated (see JP 2014-024835A).

Sample Preparation 0.1% (w/v) sirolimus suspension: it was prepared by suspending in 0.01% (w/v) hydroxypropylmethyl cellulose. Incidentally, with regard to sirolimus, that purchased from LKT Laboratories, Inc., (Catalog number: R0161) was used (which is the same in the following Examples).

Test Method

10 μL of the complete Freund's adjuvant was administered to the right upper eyelid (3 portions) of about 2 kg of male Japanese white rabbits, respectively. After 4 days from provocation, around the meibomian gland orifices of the right upper eyelid was observed by using slit lamp, a score of telangiectasia and a score of obstruction at the meibomian gland orifices were judged.

Incidentally, with regard to the score of telangiectasia, in accordance with the criteria in the following Tables 1 and 2, the eyelid margin of the upper eyelid was equally divided to three fractions of the ear side, the center portion and the nose side, the score of telangiectasia around the meibomian gland orifices was judged with regard to the respective fractions, and the sum of the scores of the three fractions was calculated as a score per one eye. Here, the presence or absence of dilation of the capillaries was judged by the state whether the capillaries which cannot be usually recognized with naked eyes can be recognized or not as a result of dilation of the diameter of the blood vessel. Also, the presence or absence of obstruction of the meibomian gland orifices was judged by the state whether the meibomian gland orifices are in a turbid or not.

TABLE 1

| Score | State of telangiectasia around meibomian gland orifices |
|---|---|
| 0 | No telangiectasia around meibomian gland orifices was recognized in opened state of eyelid |
| 1 | Dilation of several capillaries around meibomian gland orifices was recognized in opened state of eyelid |
| 2 | Moderate dilation of capillaries or slight redness around meibomian gland orifices was recognized in opened state of eyelid |
| 3 | Redness and advanced dilation of capillaries around meibomian gland orifices were recognized in opened state of eyelid |

TABLE 2

| Score | Grade | State of obstruction at meibomian gland orifices |
|---|---|---|
| 0 | None | No signs/findings |
| 1 | Slight | Obstructions of 3 or less |
| 2 | Moderate | Obstructions of 4 to 6 |
| 3 | Advanced | Obstructions of 7 or more |

The rabbits were grouped into a physiological saline solution-administered group and a 0.1% sirolimus suspension-administered group, and tested with 7 or 8 eyes in each group so that fluctuation of the average value of the respective scores became small. After $5^{th}$ day from provocation, a physiological saline solution (50 μL/eye, twice a day) or a 0.1% sirolimus suspension (50 μL/eye, twice a day) was dropped into the right eye for 10 days. After $11^{th}$ and $15^{th}$ days from provocation, around the meibomian gland orifices of the right upper eyelid was observed by using a slit lamp, whereby the score of telangiectasia was judged and the number of the obstructive orifices was measured.

Test Results

Test results (score of telangiectasia and average value of number of obstructive orifices) are shown in Table 3.

TABLE 3

|  | Score of telangiectasia | | Score of obstruction of orifices | |
|---|---|---|---|---|
|  | $11^{th}$ day after | $15^{th}$ day after | $11^{th}$ day after | $15^{th}$ day after |
| Physiological saline-administered group (N = 8) | 5.0 | 5.1 | 3.8 | 4.4 |
| 0.1% Sirolimus suspension-administered group (N = 7) | 2.1 | 2.1 | 2.3 | 1.3 |

Consideration 0.1% sirolimus suspension decreased the score of telangiectasia around the meibomian gland orifices and the number of the obstructive orifices. That is, since sirolimus resolved these meibomian gland abnormalities, it could be shown that the present compound or a pharmaceutically acceptable salt thereof has a treatment effect to MGD.

Test Using HR-AD Feed Fed Hairless Mouse

It has been known that a HR-AD feed is fed to Hos: HR-1 series hairless mouse, obstruction of the meibomian gland orifices similar to the signs/findings of MGD could be recognized (Japanese Patent Application No. 2012-137778). Thus, effects of sirolimus and deforolimus which are representative examples of the present compounds on the obstruction were investigated.

Sample Preparation 0.1% (w/v) sirolimus suspension: it was prepared by suspending in 0.01% (w/v) hydroxypropylmethyl cellulose.
0.1% (w/v) deforolimus suspension: it was prepared by suspending in 0.01% (w/v) hydroxypropylmethyl cellulose. Incidentally, deforolimus used in the present test was prepared according to the method described in JP 2005-516065A.

Test Method

Six-weeks old male Hos: HR-1 series hairless mice were grouped into 5 mice of a normal feed fed group (CRF-1 feed, available from Oriental Yeast Co., Ltd.) and 15 mice of a HR-AD feed fed group (available from Nosan Corporation), and fed the normal feed or the HR-AD feed, respectively, which were spontaneously taken. After $28^{th}$ day from initiation of the feeding, the meibomian gland orifices were observed by using a slit lamp, and a number of obstructive orifices among the eight meibomian gland orifices at the center of the upper eyelid was measured. Incidentally, the presence or absence of obstruction of the meibomian gland orifices was judged by the state whether the meibomian gland orifices were in a turbid and raised or not (see JP 2014-023526A).

Fifteen mice of the HR-AD feed fed group were grouped into a physiological saline solution-administered group, a 0.1% sirolimus suspension-administered group and a 0.1% deforolimus suspension-administered group (5 mice in each group), and from $29^{th}$ day from initiation of the feeding, the physiological saline solution (2 μL/eye, twice a day), the 0.1% sirolimus suspension (2 μL/eye, twice a day) or the 0.1% (w/v) deforolimus suspension (2 μL/eye, twice a day) were dropped to the eye for 28 days. At $42^{nd}$ day and $56^{th}$ day after initiation of the feeding, a number of obstructions of the meibomian gland orifices was measured by using a slit lamp.

Test Results

Test results are shown in Table 4.

TABLE 4

| | Number of obstructive orifices | |
|---|---|---|
| | $42^{nd}$ day after initiation of the feeding | $56^{th}$ day after initiation of the feeding |
| Non-treatment group (Normal feed fed group) | 1.2 | 0.7 |
| Physiological saline solution-administered group | 5.8 | 6.3 |

TABLE 4-continued

| | Number of obstructive orifices | |
|---|---|---|
| | $42^{nd}$ day after initiation of the feeding | $56^{th}$ day after initiation of the feeding |
| 0.1% Sirolimus suspension-administered group | 0.7 | 0.0 |
| 0.1% Deforolimus suspension-administered group | 2.7 | 2.2 |

Consideration 0.1% sirolimus suspension and 0.1% deforolimus suspension decreased the number of the obstructions of the meibomian gland orifices. That is, since sirolimus and deforolimus resolved meibomian gland abnormalities, it could be shown that the present compounds or a pharmaceutically acceptable salt thereof have a treatment effect to MGD.

Preparation Examples

The drugs of the present invention are more specifically explained by referring to Preparation examples, but the present invention is not limited by these Preparation examples alone.

Prescription example 1: Eye drop (0.1% (w/v))

| In 100 ml | |
|---|---|
| Sirolimus | 0.1 g |
| Medium chain fatty acid triglyceride (MCT) | 7.5 g |
| Benzalkonium chloride | 0.2 g |
| Tyloxapol | 1.2 g |
| Poloxamer 188 | 1 g |
| Glycerin | 22.5 g |
| Sterile purified water | q.s. |

To sterile purified water are added sirolimus and the above-mentioned components other than these, and the mixture is thoroughly mixed to prepare an eye drop. Characteristics of the present eye drop is an emulsion. By changing the formulation amount of the sirolimus, eye drops with the concentration of the sirolimus of 0.05% (w/v), 0.5% (w/v) or 1% (w/v) can be prepared.

Prescription example 2: Eye drop (0.1% (w/v))

| In 100 ml | |
|---|---|
| Deforolimus | 0.1 g |
| Medium chain fatty acid triglyceride (MCT) | 7.5 g |
| Benzalkonium chloride | 0.2 g |
| Tyloxapol | 1.2 g |
| Poloxamer 188 | 1 g |
| Glycerin | 22.5 g |
| Sterile purified water | Suitable amount |

To sterile purified water are added deforolimus and the above-mentioned components other than these, and the mixture is thoroughly mixed to prepare an eye drop. Characteristics of the present eye drop is an emulsion. By changing the formulation amount of the deforolimus, eye drops with the concentration of the deforolimus of 0.05% (w/v), 0.5% (w/v) or 1% (w/v) can be prepared.

Prescription example 3: Ophthalmic ointment or ointment (excluding ophthalmic ointment) (1% (w/w))

| In 100 g | |
|---|---|
| Sirolimus | 1 g |
| Liquid paraffin | q.s. |
| White petrolatum | q.s. |

Sirolimus is added to uniformly melt white petrolatum and liquid paraffin, and the mixture is thoroughly mixed and then gradually cooled to prepare an ophthalmic ointment or an ointment (excluding an ophthalmic ointment). By changing the formulation amount of the sirolimus, an ophthalmic ointment or an ointment (excluding an ophthalmic ointment) with the concentration of the sirolimus of 0.05% (w/w), 0.1% (w/w) or 0.5% (w/w) can be prepared.

Prescription example 4: Ophthalmic ointment or ointment (excluding ophthalmic ointment) (1% (w/w))

| In 100 g | |
|---|---|
| Deforolimus | 1 g |
| Liquid paraffin | q.s. |
| White petrolatum | q.s. |

Deforolimus is added to uniformly melt white petrolatum and liquid paraffin, and the mixture is thoroughly mixed and then gradually cooled to prepare an ophthalmic ointment or an ointment (excluding an ophthalmic ointment). By changing the formulation amount of the deforolimus, an ophthalmic ointment or an ointment (excluding an ophthalmic ointment) with the concentration of the deforolimus of 0.05% (w/w), 0.1% (w/w) or 0.5% (w/w) can be prepared.

UTILIZABILITY IN INDUSTRY

As can be clearly seen from the results of the tests using complete Freund's adjuvant administered rats and HR-AD feed fed hairless mice, sirolimus and deforolimus suppressed obstruction of the meibomian gland, so that the present compounds or a pharmaceutically acceptable salt thereof are useful as a prophylactic and/or therapeutic agent for MGD.

The invention claimed is:

1. A method for decreasing a number of obstructions of meibomian gland orifices in a mammalian subject, the method comprising administering to the mammalian subject an eye drop comprising 0.01 to 0.5% (w/v) of sirolimus or a pharmaceutically acceptable salt thereof as a sole active ingredient, wherein the eye drop is administered to an eye of the mammalian subject 1 to 2 times per day.

2. The method according to claim 1, wherein the obstructions of meibomian gland orifices are a cause of the dry eye.

3. The method according to claim 1, wherein the eye drop is a suspension or an emulsion.

4. The method according to claim 1, wherein the eye drop is a suspension.

5. The method according to claim 1, wherein the eye drop is an aqueous suspended composition.

6. The method according to claim 1, wherein the eye drop is administered to the eye of the mammalian subject 1 time per day.

7. A method for suppressing obstruction of meibomian gland in a mammalian subject, the method comprising administering to the mammalian subject an eye drop comprising 0.01 to 0.5% (w/v) of sirolimus or a pharmaceutically acceptable salt thereof as a sole active ingredient, wherein the eye drop is administered to an eye of the mammalian subject 1 to 2 times per day.

8. The method according to claim 7, wherein the obstruction of meibomian gland is a cause of the dry eye.

9. The method according to claim 7, wherein the eye drop is a suspension or an emulsion.

10. The method according to claim 7, wherein the eye drop is a suspension.

11. The method according to claim 7, wherein the eye drop is an aqueous suspended composition.

12. The method according to claim 7, wherein the eye drop is administered to the eye of the mammalian subject 1 time per day.

* * * * *